(12) United States Patent
Graßl et al.

(10) Patent No.: US 10,213,591 B2
(45) Date of Patent: Feb. 26, 2019

(54) PLUG-IN CONNECTOR FOR MEDICAL TUBES

(75) Inventors: Thomas Graßl, Lübeck (DE); Kirill Koulechov, Timmendorfer Strand (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 2314 days.

(21) Appl. No.: 12/493,378

(22) Filed: Jun. 29, 2009

(65) Prior Publication Data

US 2010/0056933 A1  Mar. 4, 2010

(30) Foreign Application Priority Data

Aug. 29, 2008  (EP) .................... 08 163 270

(51) Int. Cl.
*A61M 39/12* (2006.01)
*A61B 5/022* (2006.01)
*A61M 39/10* (2006.01)
*F16L 37/092* (2006.01)

(52) U.S. Cl.
CPC ........ *A61M 39/12* (2013.01); *A61M 39/1011* (2013.01); *F16L 37/0925* (2013.01)

(58) Field of Classification Search
USPC .................. 600/490; 285/108, 921
See application file for complete search history.

(56) References Cited

U.S. PATENT DOCUMENTS

| | | | |
|---|---|---|---|
| 1,516,397 A * | 11/1924 | Mueller et al. | 285/340 |
| 3,588,149 A * | 6/1971 | Denier | 285/110 |
| 3,640,552 A | 2/1972 | Demler, Sr. et al. | |
| 4,664,427 A * | 5/1987 | Johnston | 285/340 |
| 4,733,692 A * | 3/1988 | Kotake et al. | 137/614.13 |
| 4,915,420 A * | 4/1990 | Washizu | 285/39 |
| 5,489,125 A * | 2/1996 | Hohmann | 285/81 |
| 5,549,865 A * | 8/1996 | Guests | 264/318 |
| 6,334,634 B1 | 1/2002 | Osterkil | |
| 6,471,252 B1 * | 10/2002 | Moretti et al. | 285/319 |
| 6,641,177 B1 * | 11/2003 | Pinciaro | 285/242 |
| 2001/0045749 A1 | 11/2001 | Camozzi | |
| 2004/0232696 A1 * | 11/2004 | Andre | 285/319 |

(Continued)

FOREIGN PATENT DOCUMENTS

| | | | |
|---|---|---|---|
| EP | 0 640 358 A1 | 3/1995 | |
| EP | 1 143 185 A1 | 10/2001 | |
| EP | 1 584 348 B1 | 10/2005 | |

(Continued)

*Primary Examiner* — Michael R Bloch
(74) *Attorney, Agent, or Firm* — McGlew and Tuttle, P.C.

(57) ABSTRACT

A second part extending around a first part in a plugged-together state. The second part has snap-in element with an inwardly protruding projection for meshing with a complementary recess on an outer surface of the first part to hold the second part fixed in the axial direction on the first part. Both parts have a central passage opening. One part has an end area expanding towards the outlet opening in a connection area, and the other part is connected to an elastic section, arranged in its interior. The front end of the elastic section is pressed into contact with the expanded end area of the opposite part. The projection of the snap-in element maintains the first and second parts meshed together, so that the elastic section exerts a sealing function due to the pressure on the expanding end area.

19 Claims, 5 Drawing Sheets

(56) References Cited

U.S. PATENT DOCUMENTS

2007/0038133 A1\* 2/2007 Kishimoto et al. .......... 600/490
2008/0018106 A1 1/2008 Paluncic

FOREIGN PATENT DOCUMENTS

| EP | 1 636 521 | 3/2006 |
| GB | 2 343 723 A | 5/2000 |
| WO | 2005/037362 A1 | 4/2005 |

\* cited by examiner

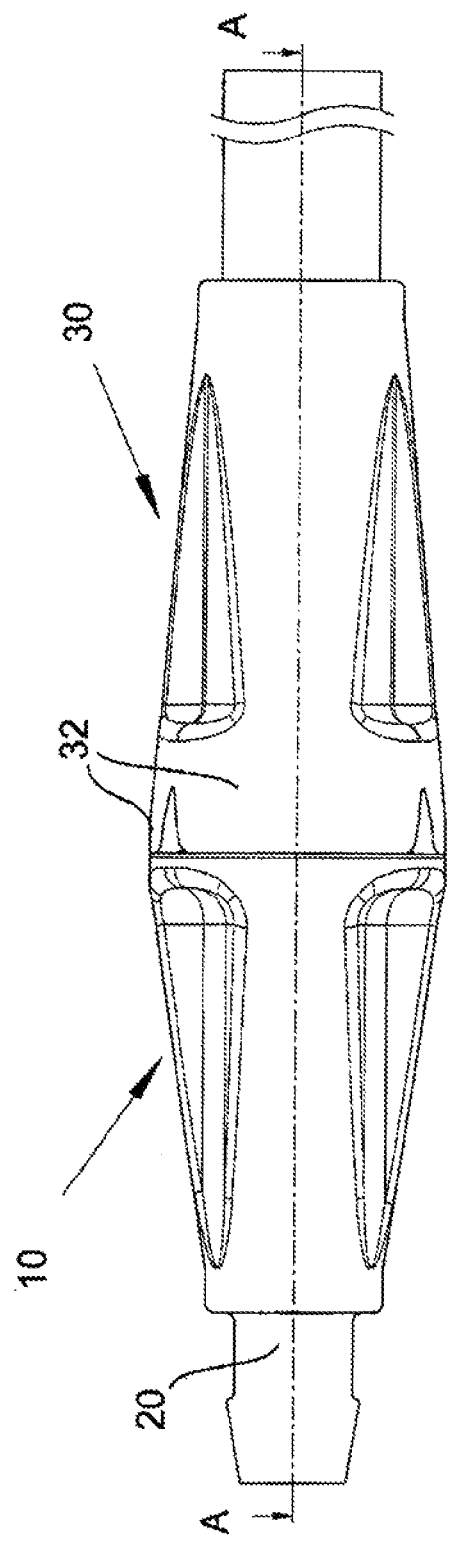
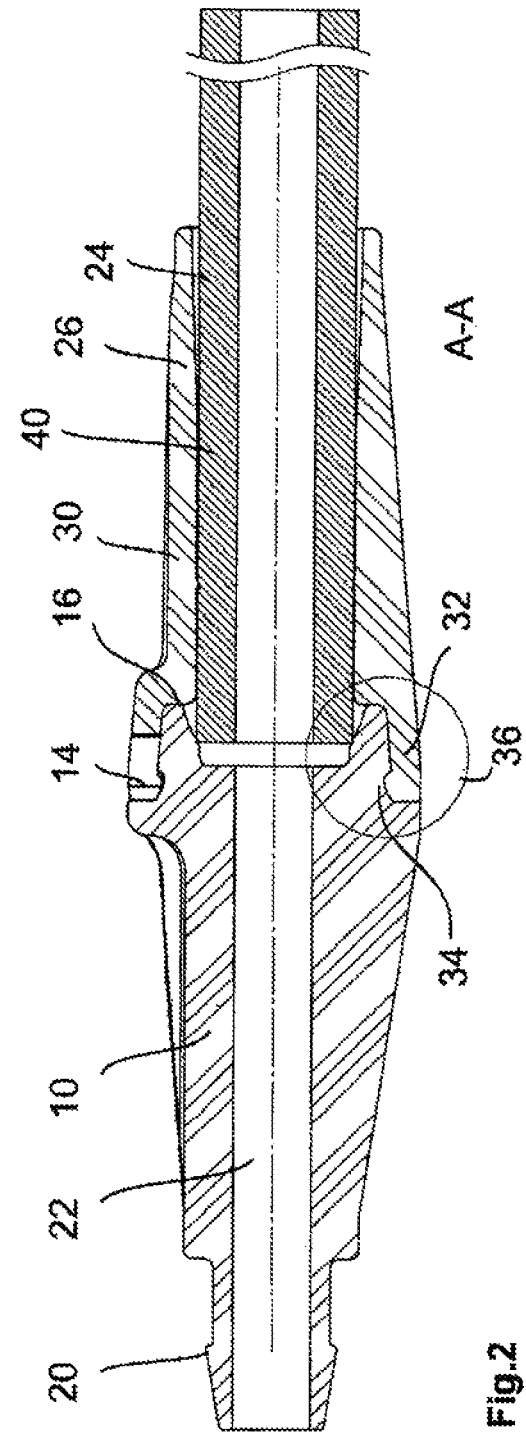

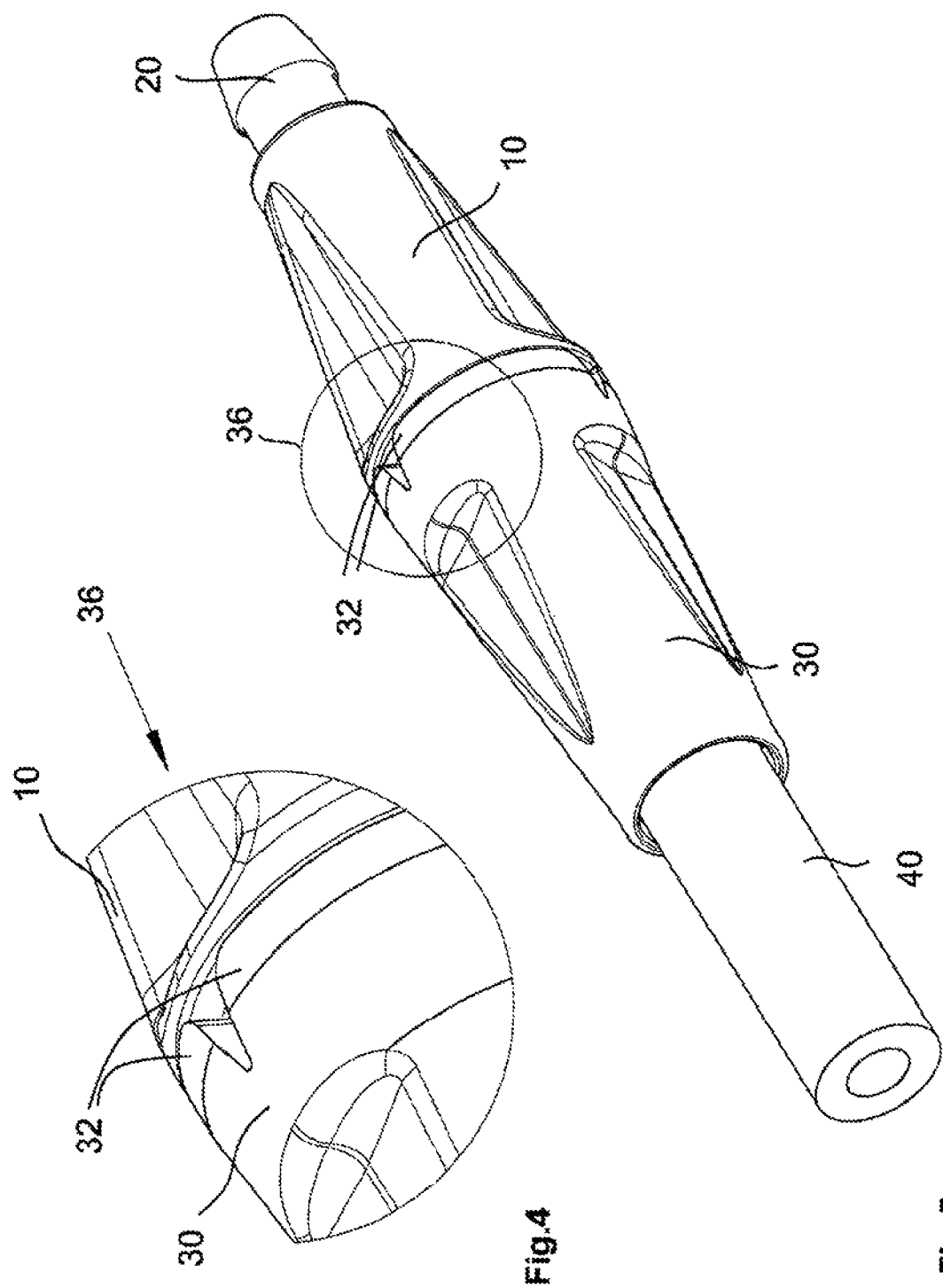

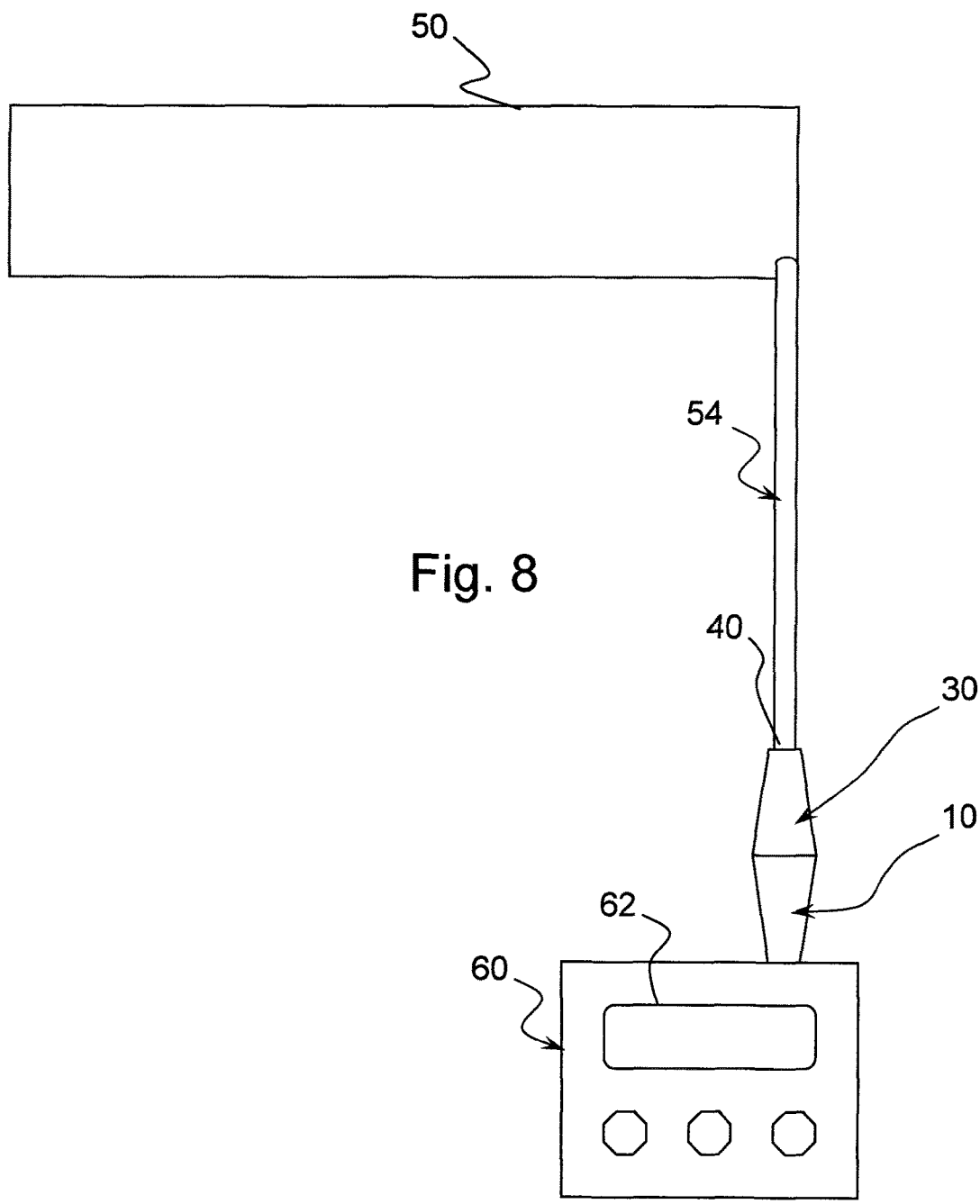

PLUG-IN CONNECTOR FOR MEDICAL TUBES

CROSS REFERENCE TO RELATED APPLICATIONS

This application claims the benefit of priority under 35 U.S.C. § 119 of European Patent Application EP 08 2008 163 270.5 filed Aug. 29, 2008, the entire contents of which are incorporated herein by reference.

FIELD OF THE INVENTION

The present invention pertains to a plug-in connector for medical tubes.

BACKGROUND OF THE INVENTION

Medical plug-in connectors are used, for example, to connect a sphygmomanometer cuff to a blood pressure analysis unit in noninvasive blood pressure measurement applications.

A plug-in connector for pressure and vacuum tubes is known from U.S. Pat. No. 3,640,552. The prior-art connector has an inner plug-in part and an outer plug-in part, which extends around a front end area of the inner plug-in part in the attached state and is provided with protruding elastic snap-in hooks with radially inwardly protruding projections, which are bent at first radially outwardly when pushed over the inner plug-in part and then bring about a connection of the two plug-in parts with one another by snapping into corresponding depressions in the outer surface of the inner plug-in part. The elastic snapping in of the snap-in hooks with their protrusion in the depressions brings about axial fixation of the two plug-in parts in relation to one another. A circumferential sealing projection is provided in the interior of the passage as a freely protruding part of the inner plug-in part such that it comes into contact with a sealing projection in the inner passage of the outer plug-in part when the snap-in hook snaps in and establishes sealing by pressing on between the plug-in parts. The tubes to be connected by the plug-in connector are introduced each into the end of the plug-in part facing away from the connection area and fixed in the interior thereof, the tubes not reaching into the connection area of the two plug-in parts. Seals of complicated designs of each tube and the corresponding plug-in part and the two plug-in parts among each other are present.

A plug-in connector for medical tubes, which likewise has an inner plug-in part and an outer plug-in part, is known from EP 1 584 348 B1. At its end facing the connection area, the outer plug-in part has an inlet section designed as a hollow cylinder and a radially outwardly expanded, rounded holding section, which axially adjoins same and is designed for positive-locking meshing with an outwardly protruding holding section on the inner plug-in part. The holding section on the inner plug-in part is designed such that it can slide through the inlet section in the outer plug-in part when the plug-in parts are plugged into one another and separated while one or both plug-in parts undergo elastic deformation, after which it generates meshing with elastic positive-locking connection at the inner surface of the outer plug-in part after reaching the radially expanded holding section, as a result of which a holding function and a sealing function are brought about simultaneously by the holding sections meshing with one another. The tubes to be connected by the plug-in connector are always pushed from the outside onto connecting branches provided on the ends facing away from the connection area. As a result, another sealed connection must always be provided between the respective tube and the outer end of the plug-in part in the area of this connecting branch. This makes the design of the plug-in connector on the whole complicated, because tight connections must be established both between the tubes and the respective plug-in part and between the respective plug-in parts themselves. The central passage opening of the respective plug-in connectors has a different diameter, and the internal diameter is made larger especially in the coupling area compared to the area of the plug-in connectors that is located away from the coupling. Different diameters of the passage opening of the plug-in connectors may lead to attenuation of the measured signal and hence to an inaccurate measurement result during the transmission of the measured signal especially during a noninvasive blood pressure measurement.

SUMMARY OF THE INVENTION

The object of the present invention is to overcome the drawbacks shown in the state of the art and to provide a plug-in connector that can be both manufactured and handled in a simple manner and guarantees reliable connection of the plug-in parts.

A plug-in connector for medical tubes is provided according to the present invention, which comprises a first plug-in part and a second plug-in part, wherein the second plug-in part extends around the first plug-in part in the front end area in the plugged-together state, wherein the second plug-in part has at least one forwardly protruding snap-in element, which has at its front end at least one radially inwardly protruding projection, which is provided for engaging a complementary recess in the outer surface of the first plug-in part in order to thus hold the second plug-in part fixed in the axial direction on the first plug-in part due to meshing of the projection with the recess. Furthermore, both plug-in parts have a central passage opening each. A plug-in part has an end area expanding towards the outlet opening in a connection area and the other plug-in part is connected to an elastic section, which is arranged coaxially in its interior and which protrudes into the connection area, so that the front end of the elastic section is pushed into contact with the expanded end area of the opposite plug-in part when the protrusion of the at least one snap-in element holds the second plug-in part engaged with the first plug-in part, so that the elastic section exerts a sealing function due to the pressure on the expanding end area. Sealing is brought about by this pressing of the front end area of the elastic section onto the inner surface of the opposite, expanding end area due to elastic pressing and deformation of the end of the elastic section. The elastic section may be designed as an elastic tube section. The elastic tube section may be a separate tube part. In a preferred embodiment, the elastic tube section is, however, the front end of the tube introduced from behind into the corresponding plug-in part, which is a firm, full-area connection with the inner surface of the plug-in part. It is possible in this embodiment of the plug-type connection according to the present invention that the tube is integrated with one of the plug-in parts, so that no additional sealing is necessary here at this plug-in part, and it brings about at the same time a sealing function of the plug-in parts between each other.

A more reliable plug-type connection that can be separated in a simple manner is created in this manner.

The elastic section, preferably the elastic tube section or the tube, may be bonded, for example, into the inner passage of the plug-in part. As an alternative, the elastic section may be manufactured in one piece with the plug-in part, for example, by a two-component injection molding procedure, in which case the hardness (Shore hardness) of the elastic section is made lower than that of the adjoining connector component. The elastic section preferably has a Shore hardness of 60 to 80 ShA.

To achieve good sealing, the expanded end area of the plug-in part is made conical. As an alternative, the expanded end area of the plug-in part may also have a spherical design.

The internal diameter of the elastic section of the second plug-in part is advantageously equal to the internal diameter of the inner passage of the first plug-in part and to the internal diameter of a connection tube. The constant lumen resulting herefrom guarantees low-loss transmission of sound waves in the application of the plug-in connector in a noninvasive blood pressure measuring system. Better signal quality can now be achieved and the blood pressure of a patient can be detected more accurately. An application of the plug-in connector according to the present invention for a noninvasive blood pressure measuring system thus makes it possible to increase patient safety.

The present invention will be described below on the basis of an exemplary embodiment shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a top view of a first embodiment of the plug-type connection;

FIG. 2 is a sectional view through the plug-in connector along plane A-A in FIG. 1;

FIG. 4 is a perspective view of the plug-in connector of the first embodiment;

FIG. 5 is a detail view of the of the region enclosed in a circle in FIG. 4;

FIG. 8 is a schematic view (not to scale) showing a noninvasive blood pressure measuring system with the tube plug-in connector according to the invention.

DESCRIPTION OF THE PREFERRED EMBODIMENTS

Figure 3:
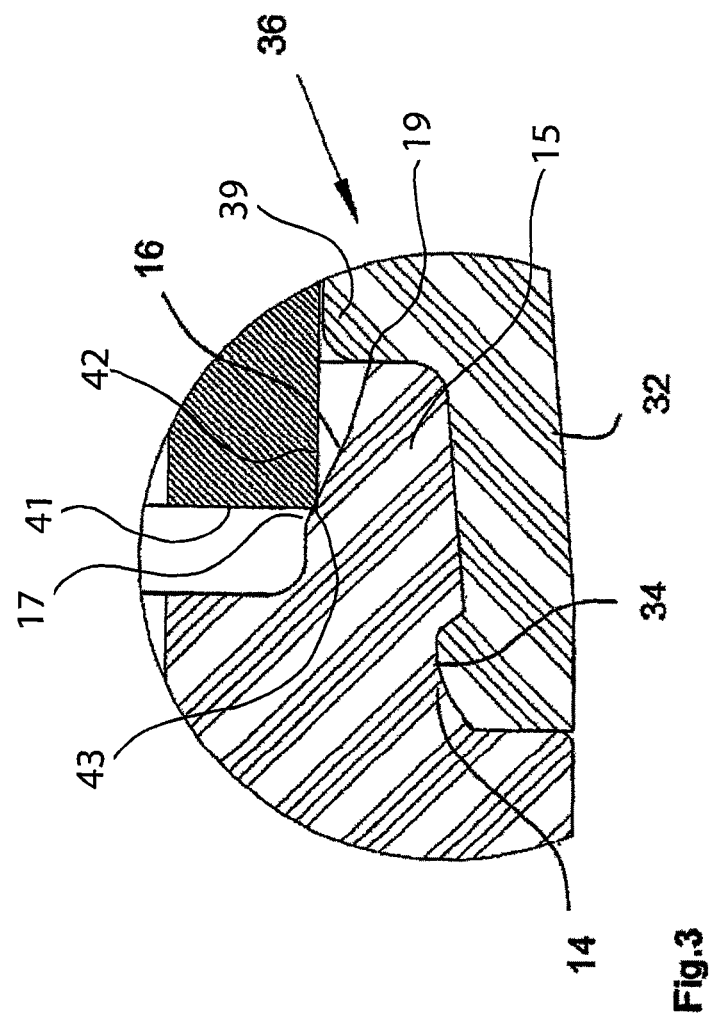
FIG. 3 is an enlarged detail of the region enclosed in a circle in FIG. 2.

Referring to the drawings in particular, the plug-in connector shown in FIGS. 1 and 2 has a first plug-in part 10 and a second plug-in part 30, which extends around the outer surface of the first plug-in part 10 with its front end. The end of the second plug-in part 30 facing a connection area 36 has snap-in elements 32, which are designed as snap-in hooks which protrude forwardly in the axial direction in the connection area 36 and have radially inwardly pointing projections 34 at their protruding end. The projections 34 are provided for meshing with a complementary recess 14 on the outer surface of first plug-in part 10. When the plug-in parts 10 and 30 are pushed into one another, the projections 34 slide on the front outer surface of the front end of the first plug-in part 10, which surface expands slightly conically in this area, as a result of which the snap-in elements 32 are bent elastically outwardly. When the projections 34 of the snap-in elements 32 reach the recess 14 in the outer surface of the first plug-in part 10, they are pushed elastically in there in order to thus fix the second plug-in part 30 to the first plug-in part 10.

An elastic section 40 is integrated in the inner passage opening 26 of the second plug-in part 30. The elastic section 40 is designed as an elastic tube section, the elastic section 40 being bonded in this exemplary embodiment into the inner passage opening 26 of the second plug-in part 30. As an alternative, the elastic section 40 may be made in one piece with the second plug-in part 30, in which case the material of the elastic section 40 is preferably manufactured with a lower Shore hardness than the second plug-in part 30. The elastic section 40 advantageously has a Shore hardness of 60 to 80 ShA. The material of the elastic section 40 may consist of thermoplastic elastomer or thermoplastic polyurethane in this embodiment. One of the two plug-in parts 10 or 30 may be manufactured from an elastic material with a lower Shore hardness than the other plug-in part 10 or 30 in another embodiment variant.

The end located opposite the connection area 36 of the first plug-in part 10 has a fastening piece 20 for pushing on a tube. The internal diameter of an inner passage 24 of the elastic section 40 arranged in the second plug-in part 30 is advantageously equal to the internal diameter of an inner passage 22 of the first plug-in part 10. The internal diameter of the inner passages 22 and 24 of the two plug-in parts 10 and 30 correspond to the internal diameter of the tube to be connected to the fastening piece 20. The constant lumen resulting therefrom guarantees low-loss sound wave transmission in the application of the plug-in connector in a noninvasive blood pressure measuring system.

The front end 41 of the elastic section 40 fastened in the second plug-in part 30 protrudes over the front end 39 of the second plug-in part 30. The end area 15 of the first plug-in part 10 facing the connection area 36 has an end area 16 expanding axially conically towards the connection area 36, the internal diameter of the expanded end area 16 at the outermost end 19 being larger than the external diameter of the protruding elastic section 40 and the internal diameter of the other end 17 of the conically expanded end area 16 farther in the interior of the inner passage 22 of the first plug-in part 10 being smaller than the external diameter of the elastic section 40. The elastic section 41 having a circumferential surface 42 extending circumferentially around an outside of the elastic section 40. The circumferential surface 42 intersecting with the front end/axially facing surface 41 at an edge 43. The front end 41 and/or edge 43 of the elastic section 40 is pressed hereby in the snapped-in position of the snap-in elements 32 shown in FIGS. 1 through 3 against the inner surface of the conically expanded end area 16, as a result of which an annular circumferential pressing surface is formed, which exerts a sealing function in order to thus connect the inner passage 22 of the first plug-in part 10 in a sealed manner to the inner passage 24 of the elastic section 40. As an alternative, the expanded end area 16 of the first plug-in part 10 may also have a spherical design.

FIGS. 4 and 5 show a perspective view of the plug-type connection in the plugged-together state. The second plug-in part 30 is provided with its integrated elastic section 40, which is again designed as an elastic tube section. The end located opposite the connection area 36 of the first plug-in part 10 has a fastening piece 20 for pushing on a tube. It becomes clear from the perspective view that the snap-in elements 32 are cylinder segment-shaped areas of the front end of the second plug-in part 30, three cylinder segments in this case, which form a circumferential angle of nearly 120° and are each separated from each other by only small incisions in the front end area of the second plug-in part 30.

Figure 6:
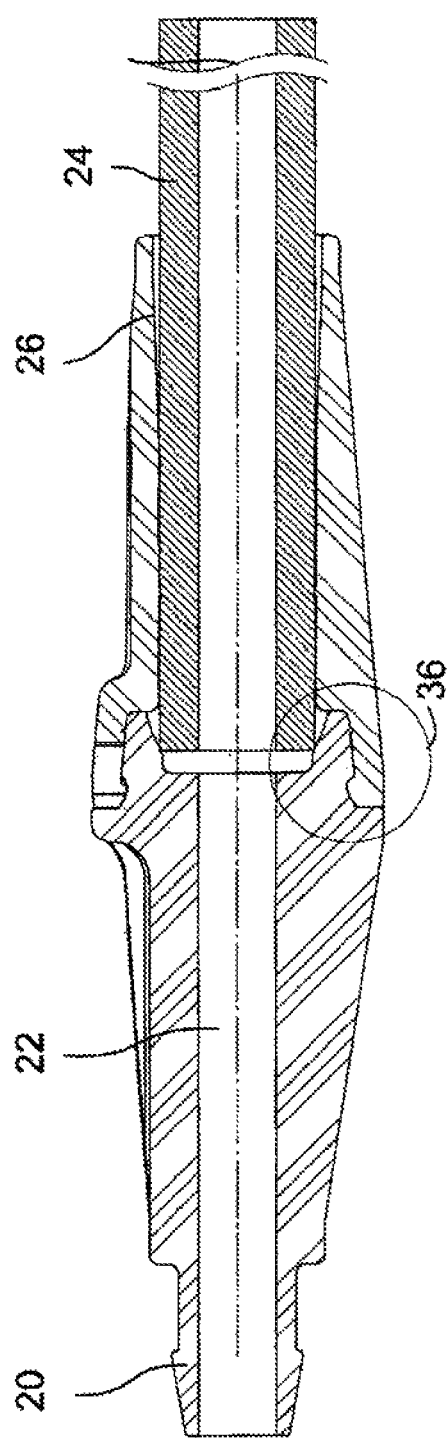
FIG. 6 is a section corresponding to FIG. 2 of a plug-in connector according to a second embodiment.
Figure 7:
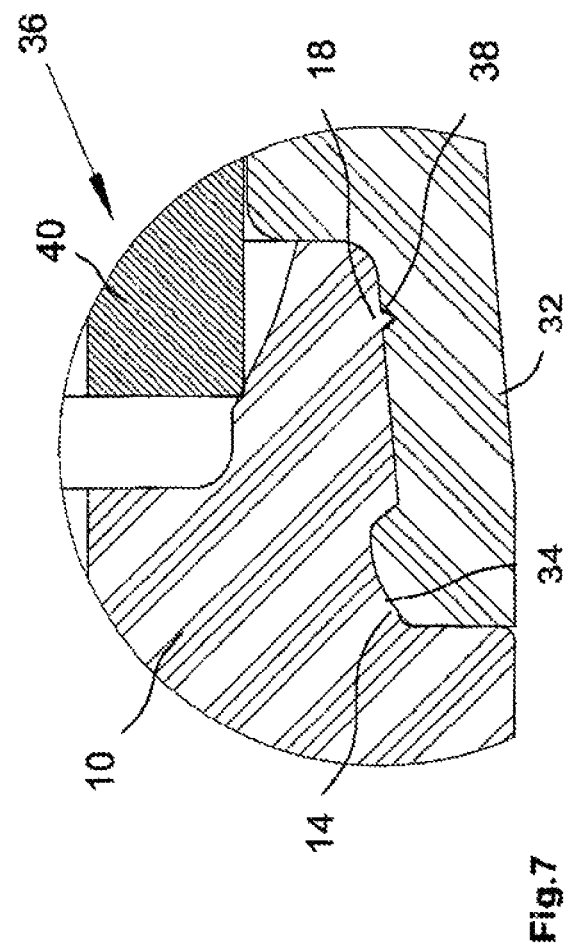
FIG. 7 is an enlarged detail view of the detail enclosed in a circle in FIG. 6.

FIGS. 6 and 7 show views corresponding to FIGS. 2 and 3 in a second embodiment, which corresponds in all features to the first exemplary embodiment, but additionally has a circumferential groove 38 (see FIG. 7) on the inner surface of the snap-in elements 32. A burr 18, which is complementary to the circumferential groove 38, is formed on the outer surface of the front end area of the first plug-in part 10. The positive-locking meshing of the burr 18 with the groove 38 ensures a further snapping in and an increase in the holding force of the plug-type connection. To separate the connection, a pulling force must be exerted on the plug-in parts 10, 30 axially away from one another, and a sufficient elastic deformation of the snap-in elements 32 and of the front end area of the first plug-in part 10, which leads to separation of the snap-in connection, occurs when a threshold force is exceeded.

The elastic section 40 is integrated in the second plug-in part 30 in the embodiments shown. However, it is, conversely, also possible to provide the elastic section 40 in the first plug-in part 10 and to arrange the opposite conical expansion for pressing on the elastic section 40 in the second plug-in part 30.

FIG. 8 shows a medical system, in particular a noninvasive blood pressure measuring system with the medical tube plug-in connector comprising a first plug-in part 10 and a second plug-in part 30 connected to an elastic section 40 of a medical tube 54. A sphygmomanometer cuff 50 is provided for detecting the blood pressure. The sphygmomanometer cuff 50 is connected to the medical tube 54. A monitor 60 is provided with a compressor or the like and sensors and a processor for detected the blood pressure data analysis with a display 62 for indicating the blood pressure of the test subject. The sphygmomanometer cuff 50 is connected to the monitor 60 by a medical tube 54 and the medical tube plug-in connector.

While specific embodiments of the invention have been shown and described in detail to illustrate the application of the principles of the invention, it will be understood that the invention may be embodied otherwise without departing from such principles.

LIST OF REFERENCE NUMBERS

10 First plug-in part
14 Recess
16 End area
18 Burr
20 Fastening piece
22 Inner passage of the first plug-in part 10
24 Inner passage opening of the elastic section 40
26 Inner passage opening of the second plug-in part 30
30 Second plug-in parts
32 Snap-in element
34 Projection
36 Connection area
38 Groove
40 Elastic section

What is claimed is:

1. A medical system comprising:
a medical tube plug-in connector comprising an elastic section, a first plug-in part and a second plug-in part, wherein the second plug-in part extends around the first plug-in part in a plugged-together state, wherein the second plug-in part has at least one forwardly protruding snap-in element, which has at a front end at least one inwardly protruding projection, which is provided for engaging a complementary recess in an outer surface of the first plug-in part in order to hold the second plug-in part fixed in an axial direction on the first plug-in part due to the projection meshing with the recess, each of the first plug-in part and the second plug-in part having a central passage opening, one of the first plug-in part and the second plug-in part having a surface defining an open end area radially expanding as a function of axial position towards an outlet opening in a connection area and the other of the first plug-in part and the second plug-in part being connected to the elastic section with the elastic section arranged in an interior thereof, said open end area being in communication with one end of said central passage of said one plug-in part, the elastic section protruding into the connection area, so that an outer and axially facing front end surface of the elastic section is pressed into contact with the surface defining the expanded end area of the opposite one of the first plug-in part and the second plug-in part when the projection of the at least one snap-in element maintains the second plug-in part meshed with the first plug-in part, so that the axially facing front end surface of the elastic section exerts a sealing function due to a pressure of the elastic section on the surface defining the expanding end area;
a sphygmomanometer cuff for detecting the blood pressure;
a medical tube connected to said sphygmomanometer cuff, said central passage and said open end area of said one plug-in part being in communication with a passage of said medical tube;
a monitor for analysis and display of the blood pressure of a test subject, said sphygmomanometer cuff being connected to said monitor by said medical tube and said medical tube plug-in connector.

2. A medical system in accordance with claim 1, wherein the elastic section comprises a front end of said medical tube connected to one of the first plug-in part and the second plug-in part.

3. A medical system in accordance with claim 1, wherein:
the elastic section is made in one piece with one of the first plug-in part and the second plug-in part; and
a material of the elastic section is manufactured with a lower Shore hardness than at least one of the plug-in parts.

4. A medical system in accordance with claim 3, wherein one of the first plug-in part and the second plug-in part is manufactured from an elastic material with a lower Shore hardness than the other plug-in part; and
the elastic section consists essentially of one or more of a thermoplastic elastomer and a thermoplastic polyurethane.

5. A medical system in accordance with claim 1, wherein:
said other plug-in part has another end connected to said medical tube, an internal diameter of said elastic section is equal to an internal diameter of the passage of said medical tube, said an internal diameter of said elastic section is also equal to an internal diameter of said central passage of said one plug-in part.

6. A medical system in accordance with claim 1, wherein:
said other plug-in part is connected to said medical tube, said medical tube extending through said other plug-in part to have an end of said medical tube form said elastic section, internal and external diameters of said elastic section and said medical tube being equal, said internal diameter of said elastic section and said medical tube being equal to an internal diameter of said central passage of said one plug-in part.

7. A medical system in accordance with claim 1, wherein:
said open end radially expands completely around said central passage opening.

8. A medical system in accordance with claim 1, wherein:
said axially facing front end surface is in a plane perpendicular to an axial direction of said one plug-part;
said axially facing front end surface is at a most distal end of said elastic section;
said elastic section has a protruding end protruding past a portion of said other plug-in part;
an internal diameter of said radially expanding open end area at an outermost end is larger than an external diameter of said protruding end of said elastic section;
an internal diameter of said expanding open end area at another end of said expanding open end area is smaller than said external diameter of said elastic section.

9. A medical system in accordance with claim 1, wherein:
said elastic section has a circumferential surface extending circumferentially around an outside of said elastic section, said circumferential surface intersecting with said axially facing front end surface at an edge;
said edge being arranged to be pressed into said expanding open end area and pressed into contact with said expanding open end area of said one plug-in part in said plugged together state to form an annular circumferential pressing surface, said pressing surface forming a seal with said open end area due to an axial pressure of said elastic section on said end area caused by said plugged together state.

10. A medical system connector in accordance with claim 1, wherein:
said expanding open end area is in communication with one end of said central passage of said one plug-in part;
said central passage of said one plug-in part has another end adapted to be in communication with the passage of the respective tube.

11. A noninvasive blood pressure measuring system process comprising the steps of:
providing a medical tube plug-in connector comprising an elastic section, a first plug-in part and a second plug-in part, wherein the second plug-in part extends around the first plug-in part in a plugged-together state, wherein the second plug-in part has at least one forwardly protruding snap-in element, which has at a front end at least one inwardly protruding projection, which is provided for engaging a complementary recess in an outer surface of the first plug-in part in order to hold the second plug-in part fixed in an axial direction on the first plug-in part due to the projection meshing with the recess, each of the first plug-in part and the second plug-in part having a central passage opening, one of the first plug-in part and the second plug-in part having a surface defining an open end area radially expanding as said open end area axially extends towards an outlet opening in a connection area and the other of the first plug-in part and the second plug-in part being connected to the elastic section with the elastic section arranged in an interior thereof, said open end area being in communication with one end of said central passage of said one plug-in part, the elastic section protruding into the connection area, so that an outer and axially facing front end surface of the elastic section is pressed into contact with the surface defining the expanded end area of the opposite one of the first plug-in part and the second plug-in part when the projection of the at least one snap-in element maintains the second plug-in part meshed with the first plug-in part, so that the axially facing front end surface of the elastic section exerts a sealing function due to a pressure of the elastic section on the surface defining the expanding end area;
providing a sphygmomanometer cuff for detecting a blood pressure;
providing a medical tube connected to said sphygmomanometer cuff, said central passage and said open end area of said one plug-in part being in communication with a passage of said medical tube;
providing a monitor for analysis and display of the blood pressure of a test subject; and
connecting the sphygmomanometer cuff to said monitor by said medical tube and said medical tube plug-in connector.

12. A process in accordance with claim 11, wherein the elastic section comprises a front end of said medical tube connected to one of the first plug-in part and the second plug-in part.

13. A process in accordance with claim 11, wherein:
the elastic section is made in one piece with one of the first plug-in part and the second plug-in part; and
a material of the elastic section is manufactured with a lower Shore hardness than at least one of the first plug-in part and the second plug-in part.

14. A process in accordance with claim 13, wherein the elastic section is formed essentially of one or more of a thermoplastic elastomer and a thermoplastic polyurethane.

15. A plug-in connector for medical tubes, the plug-in connector comprising:
a first plug-in part having an outer surface defining a recess, said first plug-in part defining a central passage in communication with a passage of one of the tubes, said first plug-in part defining an outlet opening;
a second plug-in part extending around said first plug-in part in a plugged-together state, said second plug-in part having a protruding snap-in element, which has at a front end, an inwardly protruding projection provided for engaging said recess in said outer surface of said first plug-in part in order to hold said second plug-in part fixed in an axial direction on said first plug-in part due to said projection meshing with the recess in said plugged together state, said second plug-in part defining a central passage in communication with a passage of another one of the tubes, said second plug-in part defining an outlet opening;
one of said first and second plug-in parts having an end area defining an expanding opening radially, said opening expanding as the expanding opening axially extends towards a respective outlet opening;
an elastic section connected to the other of said first and second plug-in parts, said elastic section having a front axially facing surface, said front axially facing surface being arranged to be pressed into said expanding opening and pressed into contact with said expanding opening of said one plug-in part in said plugged together state, said front axially facing surface forming a seal with said end area due to an axial pressure of said elastic section on said end area caused by said plugged together state.

16. A plug-in connector in accordance with claim 15, wherein:
the other plug-in part has another end connected to one of the medical tubes, an internal diameter of said elastic section is equal to an internal diameter of the passage of the one medical tube, said an internal diameter of said elastic section is also equal to an internal diameter of said central passage of said one plug-in part.

17. A plug-in connector in accordance with claim 15, wherein:
said front axially facing surface is in a plane perpendicular to an axial direction of said other of said plug-part;
said front axially facing surface is at a most distal end of said elastic section;
said elastic section has a protruding end protruding past a portion of said other plug-in part;
an internal diameter of said expanding opening at an outermost end is larger than an external diameter of said protruding end of said elastic section;
an internal diameter of said expanding opening at another end of said expanding opening is smaller than said external diameter of said elastic section.

18. A plug-in connector in accordance with claim 15, wherein:
said elastic section has a circumferential surface extending circumferentially around an outside of said elastic section, said circumferential surface intersecting with said front axially facing surface at an edge;
said edge being arranged to be pressed into said expanding opening and pressed into contact with said expanding opening of said one plug-in part in said plugged together state to form an annular circumferential pressing surface, said pressing surface forming a seal with said end area due to an axial pressure of said elastic section on said expanding opening caused by said plugged together state.

19. A plug-in connector in accordance with claim 15, wherein:
said expanding opening is in communication with one end of said central passage of said one plug-in part;
said central passage of said one plug-in part has another end adapted to be in communication with the passage of the respective tube.

* * * * *